US007384409B2

(12) United States Patent
Fischer et al.

(10) Patent No.: US 7,384,409 B2
(45) Date of Patent: Jun. 10, 2008

(54) DISPOSABLE CASSETTE

(75) Inventors: Michael Fischer, Zwickau (DE); Uwe Lapp, Butzbach (DE); Stephan Frey, Frankfurt (DE)

(73) Assignee: Fresenius Medical Care Deutschland GmbH, Homburg (DE)

( * ) Notice: Subject to any disclaimer, the term of this patent is extended or adjusted under 35 U.S.C. 154(b) by 705 days.

(21) Appl. No.: 10/879,355

(22) Filed: Jun. 30, 2004

(65) Prior Publication Data

US 2005/0010135 A1 Jan. 13, 2005

(30) Foreign Application Priority Data

Jul. 8, 2003 (DE) ................................ 103 30 804

(51) Int. Cl.
*A61M 1/00* (2006.01)

(52) U.S. Cl. ........................ 604/30; 600/573; 600/575; 600/580; 422/102

(58) Field of Classification Search .................. 604/34, 604/30, 408, 409, 410; 422/102; 424/70; 417/477.2–477.14, 478, 479
See application file for complete search history.

(56) References Cited

U.S. PATENT DOCUMENTS

| | | | | |
|---|---|---|---|---|
| 4,558,792 | A * | 12/1985 | Cabernoch et al. | 215/11.3 |
| 4,786,394 | A | 11/1988 | Enzer et al. | |
| 4,871,439 | A | 10/1989 | Enzer et al. | |
| 5,096,669 | A | 3/1992 | Lauks et al. | |
| 5,328,848 | A | 7/1994 | Fong et al. | |
| 5,405,510 | A | 4/1995 | Betts et al. | |
| 5,652,149 | A | 7/1997 | Mileaf et al. | |
| 5,820,825 | A | 10/1998 | Weinzierl et al. | |
| 6,068,751 | A * | 5/2000 | Neukermans | 204/601 |
| 6,171,238 | B1 * | 1/2001 | Klimes et al. | 600/345 |
| 6,743,201 | B1 | 6/2004 | Dönig et al. | |
| 2003/0023389 | A1 | 1/2003 | Rothe et al. | |
| 2003/0153844 | A1 * | 8/2003 | Smith et al. | 600/573 |
| 2004/0002161 | A1 * | 1/2004 | Sin | 436/163 |
| 2005/0054078 | A1 * | 3/2005 | Miller et al. | 435/287.1 |

FOREIGN PATENT DOCUMENTS

| | | |
|---|---|---|
| AT | 71 726 B | 2/1992 |
| DE | 42 27 338 | 2/1994 |
| DE | 198 14 695 C2 | 10/1999 |
| DE | 199 03 705 | 7/2000 |
| DE | 101 37 565 | 3/2003 |
| DE | 102 39 597 | 3/2004 |
| EP | 0 381 501 | 8/1990 |
| WO | 97/03355 | 1/1997 |

* cited by examiner

*Primary Examiner*—Joseph S. Del Sole
*Assistant Examiner*—Aarti Bhatia
(74) *Attorney, Agent, or Firm*—Jacobson Holman PLLC

(57) ABSTRACT

A disposable cassette that is configured as a replaceable component of an analysis instrument has integrated therein a sample inlet and fluid paths. At least one container with a liquid, for example a calibration fluid, and at least one waste container are integrated in the disposable cassette.

17 Claims, 2 Drawing Sheets

DISPOSABLE CASSETTE

BACKGROUND OF THE INVENTION

1. Field of Invention

The invention relates to a disposable cassette that is configured as a replaceable component of an analysis instrument.

2. Description of the Prior Art

Disposable plastic articles with fluid carrying passages are frequently used in medical equipment. Corresponding cassette systems have proven their worth here as alternatives to conventional hose systems. The corresponding fluid paths are formed in these cassette systems. The fluid flowing through the fluid paths is introduced by means of corresponding actuators. For instance, valves are, for example, used via which the fluid paths are switched open or are closed. On the other hand, pumps for the transport of the fluid are integrated in such cassette systems. In the field of medical application, disposable cassettes are already known in which a rigid part is provided in which passages and chambers are let in. This rigid part is covered by a continuously flexible film. In accordance with DE 102 39 597, this flexible film is formed by flexibly formed regions in the rigid part, with the rigid and flexible regions being able to be manufactured in one piece using a two-component injection molding technology.

The aforesaid cassette systems can also be used to advantage in the field of analysis technology.

SUMMARY OF THE INVENTION

It is the object of the invention to make available a disposable cassette for analysis purposes in which, for example, gases or electrolytes in whole blood, serum or urine can be measured. All liquids, i.e. the sample to be analyzed and also calibration solutions to be used correspondingly for the analysis, should remain in the disposable cassette in this process.

This object is solved in accordance with the invention as described herein. Accordingly, a sample inlet is provided in the disposable cassette which serves as a replaceable component of an analysis instrument. At least one container, preferably designed as a pouch, is integrated in the disposable cassette and has a liquid, preferably a calibration fluid, as well as at least one waste container, preferably a waste pouch, with the sample inlet and the different pouches being able to be connected to one another via fluid paths integrated in the disposable cassette.

It is the particular advantage of the blood analysis instrument using this disposable cassette in accordance with the invention that all fluid paths are located in the disposable cassette without direct contact to the analysis instrument. A further advantage consists of the fact that a plurality of measurements can be carried out with one disposable cassette. The waste pouch integrated into the cassette ensures that no liquid can leave the disposable cassette and that the disposable cassette with the liquids can be disposed of hygienically after the measurement series. It is therefore possible using the disposable cassette in accordance with the invention to fill in and to measure a sample, with the fluid located in the lines, in particular the calibration fluid, being displaced during the filling in of the sample. After the measurement of the sample, the cassette is flushed with calibration fluid so that the sample is flushed into the waste pouch with the calibration fluid. The sensors are subsequently recalibrated. The cassette is thus ready to receive a new sample. This cycle can be repeated approximately 30 times and even more frequently. The flushing capability of the port, as is preferably claimed, is of great importance in this process.

Preferred aspects of the invention result from the other embodiments of the disposable cassette as described herein.

For instance, at least one pouch is present in addition to the obligatorily provided waste pouch, for example, and contains a corresponding calibration fluid. Multiple measurements are hereby possible which, as previously recited, is also due to the fact that all fluid paths lie in a flushable manner inside the cassette and that there is admittedly a sample inlet in the cassette, but no liquid outlet. The consumed liquid is collected in the corresponding waste pouch. To the extent that two pouches provided with calibration fluid are provided, a two-point calibration is possible. Such a two-point calibration is substantially more precise than a one-point calibration.

The sample inlet made in the form of a port is advantageously closable by means of a slider. The slider can be adjustable in an automated manner by the analysis instrument into which the disposable cassette can be inserted, for example via a driver provided at the machine side. After the corresponding introduction of the sample, the disposable cassette can be closed by closing the slider to such an extent that a closed circuit is present inside the disposable cassette. At the end of the service life, the closure of the sample inlet serves to close the contaminated disposable cassette hermetically to allow it to be disposed of without risk.

In accordance with a further preferred aspect, the port is closable via a plastic flap hinged via a film hinge and sealingly pressable with the rim of the port via the aforesaid slider. A liquid-tight closure is ensured by the plastic flap.

The sample port can be lined on the interior with a flexible plastic material. This flexible plastic material is preferably the flexible plastic material which is provided for the limitation of the fluid paths and of the recesses for the actuators and which corresponds to the embodiment in accordance with the prior application DE 102 39 597. The sample port itself can have a passage which broadens slightly conically, adjoins a first fluid path leading into the cassette in the form of a passage with a narrow lumen and is adjoined by a cylindrical connection for the connection of a luer connector. It is possible on the basis of this aspect to permit a filling of the disposable cassette through a blood capillary (diameter 1.26 to 2.7 mm) or through a needle, for example a syringe needle or a cannula and also through a luer connector. The sample can be input in various manners due to this design of the sample port. First, the sample can be introduced via a syringe in that the luer cone is inserted and the sample is injected manually into the disposable cassette. The syringe is then removed and the plastic flap closed by means of the blocking slider.

An alternative filling possibility results via a blood capillary which is inserted into the lower, smaller cone. Since the capillary is upwardly open, the user can activate a disposable pump which interacts with the disposable cassette and which transports the desired sample into the sample passage. The capillary can then be removed and the plastic flap can be closed by means of the blocking slider.

There is a further option for the event that the sample should be removed from the interior of the syringe. A suction capillary is placed onto the luer cone of the syringe. This system is inserted into the luer cone of the sample port. Since the suction capillary is open to the side, air can follow into the syringe from the front. The user can therefore activate the disposable pump which transports the sample into the sample passage inside the disposable cassette. He can then remove the system and he can close the plastic flap by means of the blocking slider.

In accordance with an advantageous embodiment variant, a flushing passage in communication with the pouches via the fluid paths of the disposable cassette opens at the proximal end of the sample port. This permits a complete flushing of the fluid paths of the cassette. The opening region of the flushing passage is in communication with the cylindrical connection for the connection of the luer connector which is provided in the sample port. During flushing, which takes place with the port closed in a liquid-tight manner, flushing liquid therefore flows through the total port region and the flushing liquid is led into the first passage having a narrow lumen and is transported via the fluid paths integrated into the disposable cassette up to the waste pouch.

Actuators such as valves or a membrane pump are advantageously arranged in the region of the fluid paths.

BRIEF DESCRIPTION OF THE DRAWINGS

Further details and advantages of the invention will be explained in more detail with reference to an embodiment shown in the drawing. There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
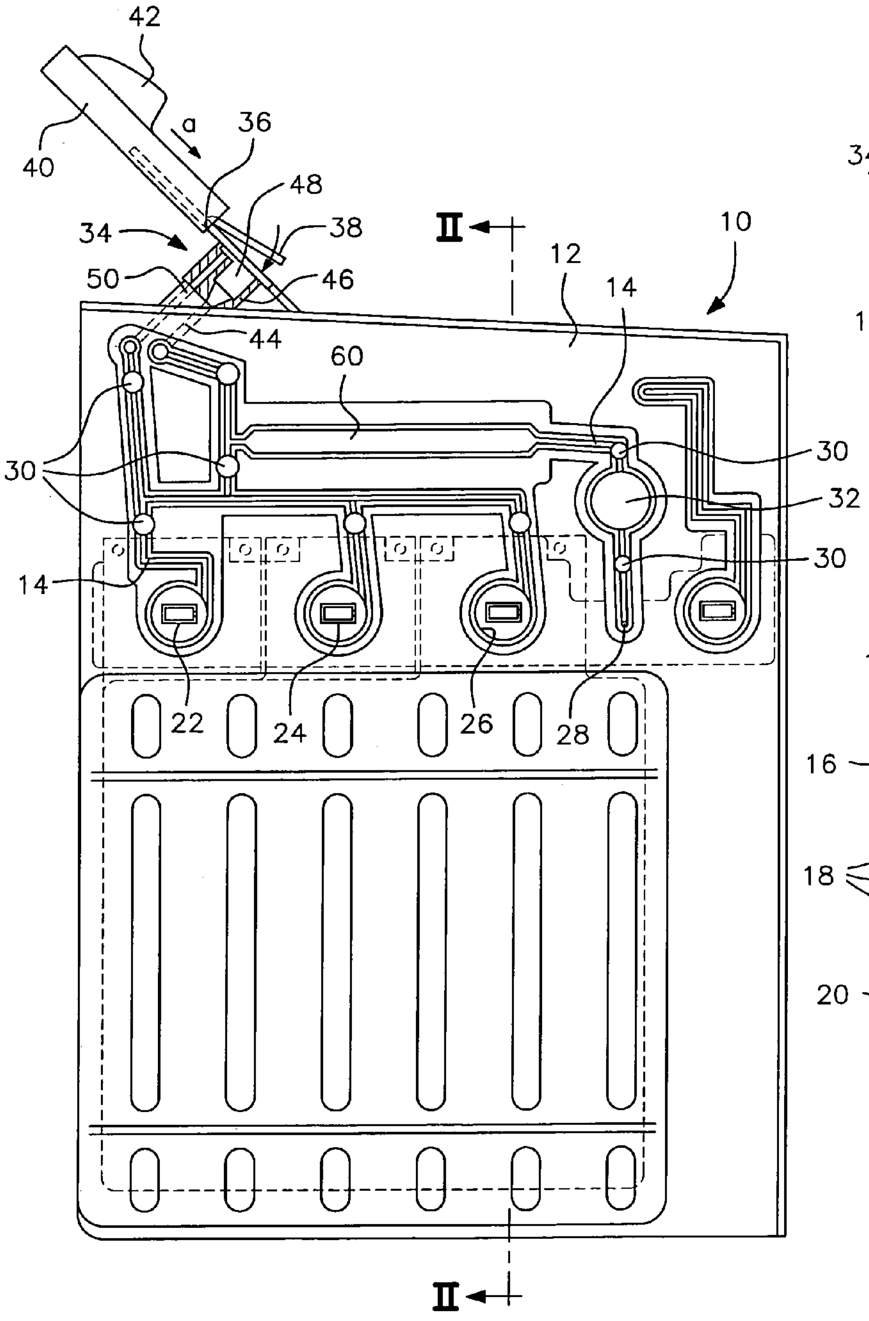
FIG. 1: the plan view of a disposable cassette in accordance with a first embodiment of the present invention, partly sectioned.
Figure 2:
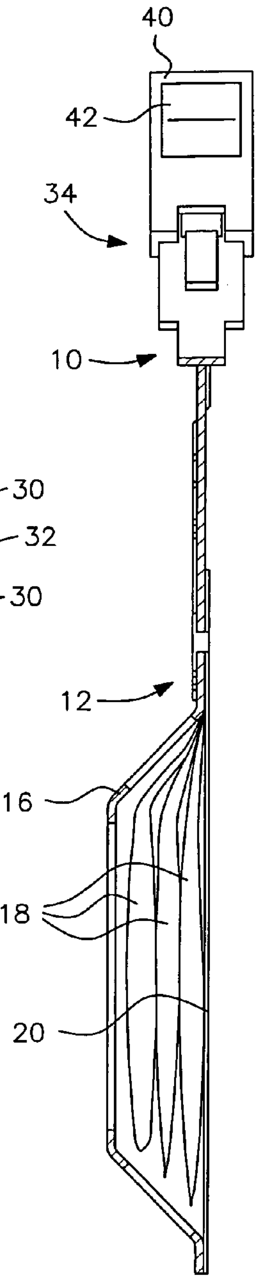
FIG. 2: a section corresponding to the section line II-II through FIG. 1.

In the disposable cassette 10 shown in FIGS. 1 and 2, a passage structure 14 is formed in a first part 12, which is made as an injection molded plastic part, for the purpose of the fluid guidance and is covered in a known manner by means of flexible elastomer material in accordance with DE 102 39 597 of the same applicant. The injection molded plastic part 12 has a shell-like recessed region 16 in which there lie 3 pouches with calibration fluid 18 and one waste pouch 20. The pouches 18 which are provided with calibration fluid and which are closed in the unused state of the disposable cassette 10 are connected to passages 14 via input regions which are to be opened directly. The waste pouch 20 is likewise connected to the passages 14 at 28. A series of actuators is present in the passage system 14 in the form of valves 30 or of a pump 32. Respective flexible plastic layers, which can be actuated via pushers on the machine side not shown in more detail here, are provided in the valves 30 or in the pump 32. Reference can be made to DE 102 39 597 for the more detailed function. Liquid can be directly transported in the passage system 14 by a corresponding control of the valves 30 or of the pump 32. The measurement path is designated by 60 in FIG. 1.

Figure 3:
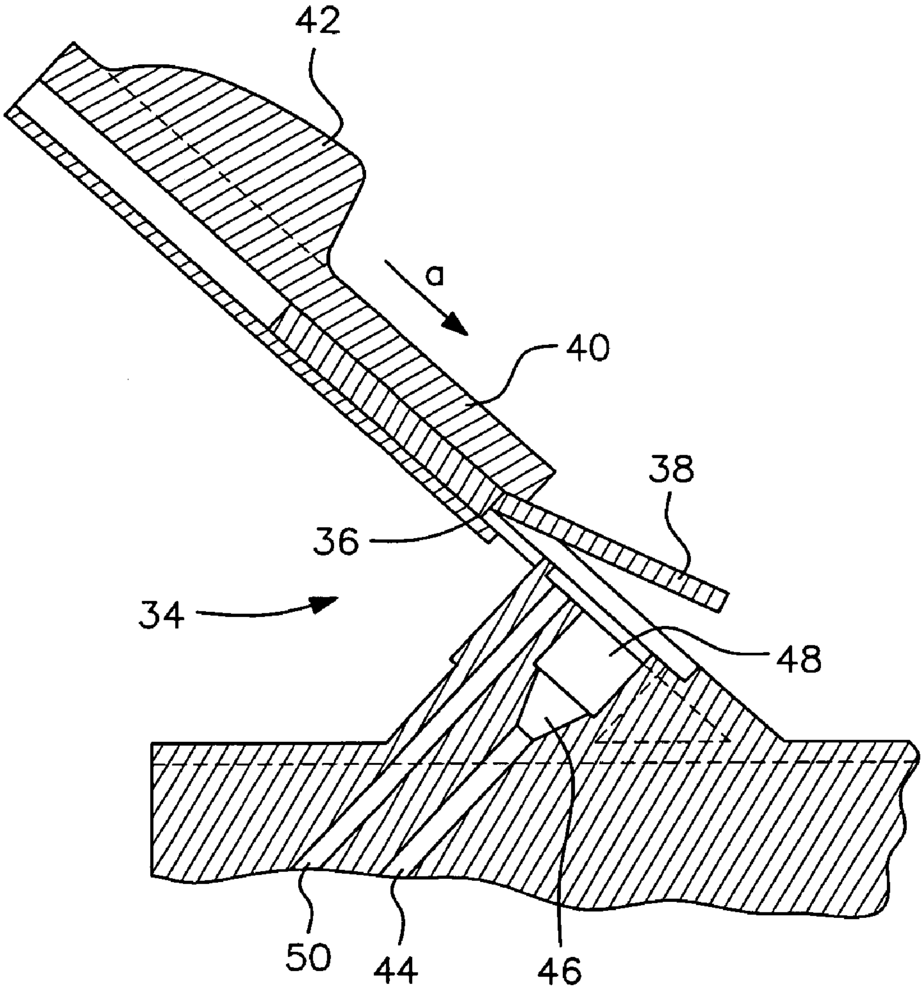
FIG. 3: an enlarged section through the sample port of the disposable cassette in accordance with FIG. 1.

A sample port 34, such as is shown in enlarged form in FIG. 3, is present for the inlet of a sample liquid, for example whole blood, serum or urine. The sample port 34 is closable in a liquid-tight manner via a plastic flap 38 hinged by means of a film hinge 36. The flap 38 is sealingly pressed onto the surface of the port 34 by pushing a slider 40 in the direction of the arrow a. The slider 40 is pushed in the opposite direction to the direction of the arrow a for the release. The slider 40 has a driver 42 via which the slider is displaceable at the machine side in or counter to the direction of the arrow. The sample port 34 is in communication with the passage system 14 via a first passage 44. A slightly conically broadening passage region 46 adjoins the passage 44 having the narrow lumen and broadens to become a cylindrical connection 48 which is made as the connection of a luer connector. The wall of this cylindrical region and of the slightly conically broadening passage 46 can be lined with flexible plastic, preferably with the same material as the passage covering. A second passage 50 having a narrow lumen extends parallel to the first passage 44, however, up to the proximal end of the sample port 34 where it is in communication with the cylindrical region 48 of the sample port 34. After closing the plastic flap 38, the whole sample port 48 can be flushed by introducing flushing liquid via the passage 50, with the consumed liquid being pumpable into the waste pouch 20 via the passage 44, the passages 14 due to the pumping effect of the pump 32.

An old blood sample or an old calibration solution can be replaced by fresh calibration solution by this flushing. The disposable cassette 10 shown in its design and its function is placed into the analysis instrument not shown in more detail here and is tightly pressed. The disposable cassettes are usually designed for a service life of 24 hours or of approximately 10 to 30 measurements. After corresponding use, the contaminated disposable cassette can be hermetically closed via closure of the slider 40 and of the plastic flap 38 and can be disposed of without risk after removal from the analysis instrument.

A cost-favorable system is provided by means of the disposable cassette in accordance with the invention in which the inlet port is suitable for samples of blood, urine or serum. The sample volume can be kept very small, with a sample volume of a maximum of 150 μl, including the volume up to the end of the sample passage, being able to be realized in the embodiment shown here. The sample port can therefore be used both for syringes and for capillaries. A favorable course of flow can be realized by means of the disposable cassette such that only a low tendency to hemolysis exists. Dead spaces are avoided in the system of the inlet port. After inputting the sample, the whole system can be flushed using an internal flushing solution. It is thereby possible to dispense with a maintenance effort for the disposable cassette. Latch positions (not shown in any more detail herein) for the port can also be realized by means of the slider 40 and here indicate a clear opened or closed state.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A disposable cassette as a replaceable component of an analysis instrument, comprising an integrated configuration of least one sample inlet port, at least one membrane pump, valves, a measurement path and fluid paths, at least one container with a liquid, at least one waste container, and a flushing passage in communication with the liquid container and the waste container via the fluid paths, the flushing passage having an inlet opening at a proximal end of the sample inlet port.

2. The disposable cassette in accordance with claim 1, wherein the cassette includes at least two containers with calibration fluid.

3. The disposable cassette in accordance with claim 1, wherein the sample inlet port is closable by a slider.

4. The disposable cassette in accordance with claim 3, wherein the sample inlet port is closable via a plastic flap which is hinged via a film hinge and which can be pressed sealingly with a rim of the port via the slider.

5. The disposable cassette in accordance with claim 1, wherein an interior of the sample inlet port is lined with a flexible plastic material.

6. The disposable cassette in accordance with claim 1, wherein the sample inlet port has a passage which broadens slightly conically, adjoins a first fluid path leading into the cassette that is a passage with a narrow lumen, and is adjoined by a cylindrical connection that is configured to communicate with a luer connector.

7. The disposable cassette in accordance with claim 1, further comprising actuators that are arranged in a region of the fluid paths.

8. The disposable cassette in accordance with claim 7, wherein the actuators are membrane pumps or valves.

9. The disposable cassette in accordance with claim 1, wherein the cassette includes all fluid paths required for multiple measurements.

10. The disposable cassette in accordance with claim 1, wherein the cassette has no outlets.

11. The disposable cassette in accordance with claim 1, wherein the disposable cassette is flushable.

12. The disposable cassette in accordance with claim 11, wherein the flushing is effected through the flushing passage inlet opening.

13. The disposable cassette in accordance with claim 1, wherein the liquid is a calibration fluid.

14. The disposable cassette in accordance with claim 1, wherein the containers are pouches.

15. The disposable cassette in accordance with claim 14, wherein the pouches are constructed of multilayer aluminum foil.

16. A disposable cassette that is a replaceable component of an analysis instrument, comprising an integrated configuration of a sample inlet port having a cylindrical connection that is configured to receive a luer connector, a membrane pump, a valve, a measurement path, a plurality of fluid paths, a calibration fluid container, a waste container, and a flushing passage in communication with the waste container via the fluid paths, the sample inlet port being closable in a liquid-tight manner and the flushing passage having an inlet opening that is adjacent the sample inlet port and that is in communication with the cylindrical connection.

17. The disposable cassette according to claim 16, wherein the sample inlet port is closable by a hinged plastic flap that is configured to be sealingly pressed onto a surface of the sample inlet port.

* * * * *